United States Patent [19]

Gerhart et al.

[11] Patent Number: 5,364,839
[45] Date of Patent: Nov. 15, 1994

[54] OSTEOINDUCTIVE PHARMACEUTICAL FORMULATIONS

[75] Inventors: Tobin N. Gerhart, Brookline; Elizabeth A. Wang, Carlisle; Mary J. Kriz, Hudson, all of Mass.

[73] Assignee: Genetics Institute, Inc., Cambridge, Mass.

[21] Appl. No.: 539,756

[22] Filed: Jun. 18, 1990

[51] Int. Cl.⁵ ............................................. A61K 37/36
[52] U.S. Cl. ........................................ 514/12; 514/21; 514/8; 530/350; 530/399
[58] Field of Search .................. 530/350, 399; 514/12, 514/21, 8

[56] References Cited

U.S. PATENT DOCUMENTS

| | | |
|---|---|---|
| 4,186,448 | 2/1980 | Brekke . |
| 4,430,760 | 2/1984 | Smestad . |
| 4,440,750 | 4/1984 | Glowacki et al. . |
| 4,563,489 | 1/1986 | Urist .................... 524/21 |
| 4,596,574 | 6/1986 | Urist .................... 424/14 |
| 4,652,441 | 3/1987 | Okada ................... 514/2 |
| 4,795,804 | 1/1989 | Urist .................... 530/350 |
| 4,877,864 | 10/1989 | Wang ................... 935/13 |
| 4,902,296 | 2/1990 | Bolander et al. . |
| 4,968,590 | 11/1990 | Kuberasampath et al. . |
| 4,979,959 | 12/1990 | Guire ................... 435/176 |
| 5,013,649 | 5/1991 | Wang ................... 935/18 |
| 5,106,748 | 4/1992 | Wozney ................. 935/9 |
| 5,141,905 | 8/1992 | Rosen ................... 935/7 |

FOREIGN PATENT DOCUMENTS

| | | |
|---|---|---|
| 0166263 | 1/1986 | European Pat. Off. . |
| 322249 | 6/1989 | European Pat. Off. . |
| 0336760A2 | 10/1989 | European Pat. Off. . |
| 361896 | 4/1990 | European Pat. Off. . |
| 733665 | 5/1980 | U.S.S.R. . |
| WO88/00205 | 1/1988 | WIPO . |
| WO89/04646 | 6/1989 | WIPO . |
| WO89/10409 | 11/1989 | WIPO . |

OTHER PUBLICATIONS

Nilsson, I. et al., *The Lancet*: 1322-1326 (1960).
Brandstedt, S. et al., *Eur. Surgical Res.* 12:12-21 (1980).
Kawamura, Morio, et al., *Clinical Orthopaedics and Related Research*, 235(10): 302-310 (1988).
Wozney et al., *Science*, 242, 1528-1534, 1988.

*Primary Examiner*—F. T. Moezie
*Attorney, Agent, or Firm*—Patricia A. McDaniels; Ellen J. Kapinos; Bruce M. Eisen

[57] ABSTRACT

Osteoinductive pharmaceutical formulations comprising antifibrinolytic agents such as epsilon amino acid caproic acid or other lysine analogues or serine protease inhibitors and cartilage and/or bone inductive proteins are disclosed. These formulations are useful in the treatment of cartilage and/or bone defects.

7 Claims, No Drawings

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 2153 base pairs
        ( B ) TYPE: nucleic acid
        ( C ) STRANDEDNESS: double
        ( D ) TOPOLOGY: linear ( i i i ) HYPOTHETICAL: NO ( v i ) ORIGINAL SOURCE:
        ( A ) ORGANISM: Homo sapiens
        ( H ) CELL LINE: U2-OS osteosarcoma ( v i i ) IMMEDIATE SOURCE:
        ( A ) LIBRARY: U2-OS human osteosarcoma cDNA library
        ( B ) CLONE: U2-16

( v i i i ) POSITION IN GENOME:
        ( C ) UNITS: bp ( i x ) FEATURE:
        ( A ) NAME/KEY: CDS
        ( B ) LOCATION: 699..2063

( i x ) FEATURE:
        ( A ) NAME/KEY: matpeptide
        ( B ) LOCATION: 1647..2060

( i x ) FEATURE:
        ( A ) NAME/KEY: mRNA
        ( B ) LOCATION: 1..2153

( x i ) SEQUENCE DESCRIPTION: SEQ ID NO:1:

```
CTGGTATATT  TGTGCCTGCT  GGAGGTGGAA  TTAACAGTAA  GAAGGAGAAA  GGGATTGAAT      60

GGACTTACAG  GAAGGATTTC  AAGTAAATTC  AGGGAAACAC  ATTTACTTGA  ATAGTACAAC     120

CTAGAGTATT  ATTTTACACT  AAGACGACAC  AAAAGATGTT  AAAGTTATCA  CCAAGCTGCC     180

GGACAGATAT  ATATTCCAAC  ACCAAGGTGC  AGATCAGCAT  AGATCTGTGA  TTCAGAAATC     240

AGGATTTGTT  TTGGAAAGAG  CTCAAGGGTT  GAGAAGAACT  CAAAAGCAAG  TGAAGATTAC     300

TTTGGGAACT  ACAGTTTATC  AGAAGATCAA  CTTTTGCTAA  TTCAAATACC  AAAGGCCTGA     360

TTATCATAAA  TTCATATAGG  AATGCATAGG  TCATCTGATC  AAATAATATT  AGCCGTCTTC     420
```

```
TGCTACATCA ATGCAGCAAA AACTCTTAAC AACTGTGGAT AATTGGAAAT CTGAGTTTCA        480

GCTTTCTTAG AAATAACTAC TCTTGACATA TTCCAAAATA TTTAAAATAG GACAGGAAAA        540

TCGGTGAGGA TGTTGTGCTC AGAAATGTCA CTGTCATGAA AAATAGGTAA ATTTGTTTTT        600

TCAGCTACTG GGAAACTGTA CCTCCTAGAA CCTTAGGTTT TTTTTTTTT AAGAGGACAA         660

GAAGGACTAA AAATATCAAC TTTTGCTTTT GGACAAAA ATG CAT CTG ACT GTA           713
                                         Met His Leu Thr Val
                                        -316-315

TTT TTA CTT AAG GGT ATT GTG GGT TTC CTC TGG AGC TGC TGG GTT CTA         761
Phe Leu Leu Lys Gly Ile Val Gly Phe Leu Trp Ser Cys Trp Val Leu
    -310             -305                 -300

GTG GGT TAT GCA AAA GGA GGT TTG GGA GAC AAT CAT GTT CAC TCC AGT         809
Val Gly Tyr Ala Lys Gly Gly Leu Gly Asp Asn His Val His Ser Ser
-295             -290                 -285                     -280

TTT ATT TAT AGA AGA CTA CGG AAC CAC GAA AGA CGG GAA ATA CAA AGG         857
Phe Ile Tyr Arg Arg Leu Arg Asn His Glu Arg Arg Glu Ile Gln Arg
            -275                 -270                     -265

GAA ATT CTC TCT ATC TTG GGT TTG CCT CAC AGA CCC AGA CCA TTT TCA         905
Glu Ile Leu Ser Ile Leu Gly Leu Pro His Arg Pro Arg Pro Phe Ser
        -260                 -255                     -250

CCT GGA AAA ATG ACC AAT CAA GCG TCC TCT GCA CCT CTC TTT ATG CTG         953
Pro Gly Lys Met Thr Asn Gln Ala Ser Ser Ala Pro Leu Phe Met Leu
        -245                 -240                 -235

GAT CTC TAC AAT GCC GAA GAA AAT CCT GAA GAG TCG GAG TAC TCA GTA        1001
Asp Leu Tyr Asn Ala Glu Glu Asn Pro Glu Glu Ser Glu Tyr Ser Val
    -230                 -225                 -220

AGG GCA TCC TTG GCA GAA GAG ACC AGA GGG GCA AGA AAG GGA TAC CCA        1049
Arg Ala Ser Leu Ala Glu Glu Thr Arg Gly Ala Arg Lys Gly Tyr Pro
-215             -210                 -205                     -200

GCC TCT CCC AAT GGG TAT CCT CGT CGC ATA CAG TTA TCT CGG ACG ACT        1097
Ala Ser Pro Asn Gly Tyr Pro Arg Arg Ile Gln Leu Ser Arg Thr Thr
            -195             -190                     -185

CCT CTG ACC ACC CAG AGT CCT CCT CTA GCC AGC CTC CAT GAT ACC AAC        1145
Pro Leu Thr Thr Gln Ser Pro Pro Leu Ala Ser Leu His Asp Thr Asn
        -180                 -175                 -170

TTT CTG AAT GAT GCT GAC ATG GTC ATG AGC TTT GTC AAC TTA GTT GAA        1193
Phe Leu Asn Asp Ala Asp Met Val Met Ser Phe Val Asn Leu Val Glu
        -165                 -160                 -155

AGA GAC AAG GAT TTT TCT CAC CAG CGA AGG CAT TAC AAA GAA TTT CGA        1241
Arg Asp Lys Asp Phe Ser His Gln Arg Arg His Tyr Lys Glu Phe Arg
        -150                 -145                 -140

TTT GAT CTT ACC CAA ATT CCT CAT GGA GAG GCA GTG ACA GCA GCT GAA        1289
Phe Asp Leu Thr Gln Ile Pro His Gly Glu Ala Val Thr Ala Ala Glu
-135                 -130                 -125                     -120

TTC CGG ATA TAC AAG GAC CGG AGC AAC AAC CGA TTT GAA AAT GAA ACA        1337
Phe Arg Ile Tyr Lys Asp Arg Ser Asn Asn Arg Phe Glu Asn Glu Thr
            -115                 -110                     -105

ATT AAG ATT AGC ATA TAT CAA ATC ATC AAG GAA TAC ACA AAT AGG GAT        1385
Ile Lys Ile Ser Ile Tyr Gln Ile Ile Lys Glu Tyr Thr Asn Arg Asp
            -100                 -95                     -90

GCA GAT CTG TTC TTG TTA GAC ACA AGA AAG GCC CAA GCT TTA GAT GTG        1433
Ala Asp Leu Phe Leu Leu Asp Thr Arg Lys Ala Gln Ala Leu Asp Val
        -85                  -80                  -75

GGT TGG CTT GTC TTT GAT ATC ACT GTG ACC AGC AAT CAT TGG GTG ATT        1481
Gly Trp Leu Val Phe Asp Ile Thr Val Thr Ser Asn His Trp Val Ile
-70                  -65                  -60

AAT CCC CAG AAT AAT TTG GGC TTA CAG CTC TGT GCA GAA ACA GGG GAT        1529
Asn Pro Gln Asn Asn Leu Gly Leu Gln Leu Cys Ala Glu Thr Gly Asp
-55                  -50                  -45                     -40
```

| | | | | | | | | | | | | | | | | |
|---|---|---|---|---|---|---|---|---|---|---|---|---|---|---|---|---|
| GGA | CGC | AGT | ATC | AAC | GTA | AAA | TCT | GCT | GGT | CTT | GTG | GGA | AGA | CAG | GGA | 1577 |
| Gly | Arg | Ser | Ile | Asn | Val | Lys | Ser | Ala | Gly | Leu | Val | Gly | Arg | Gln | Gly | |
| | | | -35 | | | | | -30 | | | | | -25 | | | |
| CCT | CAG | TCA | AAA | CAA | CCA | TTC | ATG | GTG | GCC | TTC | TTC | AAG | GCG | AGT | GAG | 1625 |
| Pro | Gln | Ser | Lys | Gln | Pro | Phe | Met | Val | Ala | Phe | Phe | Lys | Ala | Ser | Glu | |
| | | | -20 | | | | | -15 | | | | | -10 | | | |
| GTA | CTT | CTT | CGA | TCC | GTG | AGA | GCA | GCC | AAC | AAA | CGA | AAA | AAT | CAA | AAC | 1673 |
| Val | Leu | Leu | Arg | Ser | Val | Arg | Ala | Ala | Asn | Lys | Arg | Lys | Asn | Gln | Asn | |
| | | | -5 | | | | | 1 | | | | | 5 | | | |
| CGC | AAT | AAA | TCC | AGC | TCT | CAT | CAG | GAC | TCC | TCC | AGA | ATG | TCC | AGT | GTT | 1721 |
| Arg | Asn | Lys | Ser | Ser | Ser | His | Gln | Asp | Ser | Ser | Arg | Met | Ser | Ser | Val | |
| | 10 | | | | 15 | | | | 20 | | | | | | 25 | |
| GGA | GAT | TAT | AAC | ACA | AGT | GAG | CAA | AAA | CAA | GCC | TGT | AAG | AAG | CAC | GAA | 1769 |
| Gly | Asp | Tyr | Asn | Thr | Ser | Glu | Gln | Lys | Gln | Ala | Cys | Lys | Lys | His | Glu | |
| | | | | 30 | | | | | 35 | | | | | 40 | | |
| CTC | TAT | GTG | AGC | TTC | CGG | GAT | CTG | GGA | TGG | CAG | GAC | TGG | ATT | ATA | GCA | 1817 |
| Leu | Tyr | Val | Ser | Phe | Arg | Asp | Leu | Gly | Trp | Gln | Asp | Trp | Ile | Ile | Ala | |
| | | | 45 | | | | | 50 | | | | | 55 | | | |
| CCA | GAA | GGA | TAC | GCT | GCA | TTT | TAT | TGT | GAT | GGA | GAA | TGT | TCT | TTT | CCA | 1865 |
| Pro | Glu | Gly | Tyr | Ala | Ala | Phe | Tyr | Cys | Asp | Gly | Glu | Cys | Ser | Phe | Pro | |
| | | 60 | | | | | 65 | | | | | 70 | | | | |
| CTT | AAC | GCC | CAT | ATG | AAT | GCC | ACC | AAC | CAC | GCT | ATA | GTT | CAG | ACT | CTG | 1913 |
| Leu | Asn | Ala | His | Met | Asn | Ala | Thr | Asn | His | Ala | Ile | Val | Gln | Thr | Leu | |
| | 75 | | | | | 80 | | | | | 85 | | | | | |
| GTT | CAT | CTG | ATG | TTT | CCT | GAC | CAC | GTA | CCA | AAG | CCT | TGT | TGT | GCT | CCA | 1961 |
| Val | His | Leu | Met | Phe | Pro | Asp | His | Val | Pro | Lys | Pro | Cys | Cys | Ala | Pro | |
| | 90 | | | | 95 | | | | | 100 | | | | | 105 | |
| ACC | AAA | TTA | AAT | GCC | ATC | TCT | GTT | CTG | TAC | TTT | GAT | GAC | AGC | TCC | AAT | 2009 |
| Thr | Lys | Leu | Asn | Ala | Ile | Ser | Val | Leu | Tyr | Phe | Asp | Asp | Ser | Ser | Asn | |
| | | | | 110 | | | | | 115 | | | | | 120 | | |
| GTC | ATT | TTG | AAA | AAA | TAT | AGA | AAT | ATG | GTA | GTA | CGC | TCA | TGT | GGC | TGC | 2057 |
| Val | Ile | Leu | Lys | Lys | Tyr | Arg | Asn | Met | Val | Val | Arg | Ser | Cys | Gly | Cys | |
| | | | 125 | | | | | 130 | | | | | 135 | | | |
| CAC | TAATATTAAA | TAATATTGAT | AATAACAAAA | AGATCTGTAT | TAAGGTTTAT | | | | | | | | | | | 2110 |
| His | | | | | | | | | | | | | | | | |
| GGCTGCAATA | AAAAGCATAC | TTTCAGACAA | ACAGAAAAAA | AAA | | | | | | | | | | | | 2153 |

( 2 ) INFORMATION FOR SEQ ID NO:2:

( i ) SEQUENCE CHARACTERISTICS:
        ( A ) LENGTH: 454 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met  His  Leu  Thr  Val  Phe  Leu  Leu  Lys  Gly  Ile  Val  Gly  Phe  Leu  Trp
-316 -315           -310                -305
Ser  Cys  Trp  Val  Leu  Val  Gly  Tyr  Ala  Lys  Gly  Gly  Leu  Gly  Asp  Asn
-300                -295                -290                     -285
His  Val  His  Ser  Ser  Phe  Ile  Tyr  Arg  Arg  Leu  Arg  Asn  His  Glu  Arg
                    -280               -275                     -270
Arg  Glu  Ile  Gln  Arg  Glu  Ile  Leu  Ser  Ile  Leu  Gly  Leu  Pro  His  Arg
               -265                -260                     -255
Pro  Arg  Pro  Phe  Ser  Pro  Gly  Lys  Met  Thr  Asn  Gln  Ala  Ser  Ser  Ala
               -250                -245                     -240
Pro  Leu  Phe  Met  Leu  Asp  Leu  Tyr  Asn  Ala  Glu  Glu  Asn  Pro  Glu  Glu
          -235                -230                     -225
Ser  Glu  Tyr  Ser  Val  Arg  Ala  Ser  Leu  Ala  Glu  Glu  Thr  Arg  Gly  Ala
-220                -215                     -210                     -205
```

Arg Lys Gly Tyr Pro Ala Ser Pro Asn Gly Tyr Pro Arg Arg Ile Gln
            -200                -195                    -190

Leu Ser Arg Thr Thr Pro Leu Thr Thr Gln Ser Pro Pro Leu Ala Ser
            -185            -180                -175

Leu His Asp Thr Asn Phe Leu Asn Asp Ala Asp Met Val Met Ser Phe
            -170            -165                -160

Val Asn Leu Val Glu Arg Asp Lys Asp Phe Ser His Gln Arg Arg His
    -155                -150                -145

Tyr Lys Glu Phe Arg Phe Asp Leu Thr Gln Ile Pro His Gly Glu Ala
-140                -135                -130                    -125

Val Thr Ala Ala Glu Phe Arg Ile Tyr Lys Asp Arg Ser Asn Asn Arg
                -120                -115                -110

Phe Glu Asn Glu Thr Ile Lys Ile Ser Ile Tyr Gln Ile Ile Lys Glu
            -105                -100                -95

Tyr Thr Asn Arg Asp Ala Asp Leu Phe Leu Leu Asp Thr Arg Lys Ala
        -90                -85                -80

Gln Ala Leu Asp Val Gly Trp Leu Val Phe Asp Ile Thr Val Thr Ser
    -75                -70                -65

Asn His Trp Val Ile Asn Pro Gln Asn Asn Leu Gly Leu Gln Leu Cys
-60                -55                    -50                    -45

Ala Glu Thr Gly Asp Gly Arg Ser Ile Asn Val Lys Ser Ala Gly Leu
            -40                    -35                    -30

Val Gly Arg Gln Gly Pro Gln Ser Lys Gln Pro Phe Met Val Ala Phe
            -25                -20                -15

Phe Lys Ala Ser Glu Val Leu Leu Arg Ser Val Arg Ala Ala Asn Lys
        -10                -5                    1

Arg Lys Asn Gln Asn Arg Asn Lys Ser Ser Ser His Gln Asp Ser Ser
 5              10                  15                  20

Arg Met Ser Ser Val Gly Asp Tyr Asn Thr Ser Glu Gln Lys Gln Ala
            25                  30                  35

Cys Lys Lys His Glu Leu Tyr Val Ser Phe Arg Asp Leu Gly Trp Gln
            40                  45                  50

Asp Trp Ile Ile Ala Pro Glu Gly Tyr Ala Ala Phe Tyr Cys Asp Gly
        55              60                  65

Glu Cys Ser Phe Pro Leu Asn Ala His Met Asn Ala Thr Asn His Ala
    70                  75                  80

Ile Val Gln Thr Leu Val His Leu Met Phe Pro Asp His Val Pro Lys
 85                  90                  95              100

Pro Cys Cys Ala Pro Thr Lys Leu Asn Ala Ile Ser Val Leu Tyr Phe
            105                 110                 115

Asp Asp Ser Ser Asn Val Ile Leu Lys Lys Tyr Arg Asn Met Val Val
            120                 125                 130

Arg Ser Cys Gly Cys His
            135

(2) INFORMATION FOR SEQ ID NO:3:

(i) SEQUENCE CHARACTERISTICS:
        (A) LENGTH: 1448 base pairs
        (B) TYPE: nucleic acid
        (C) STRANDEDNESS: double
        (D) TOPOLOGY: unknown (ii) MOLECULE TYPE: DNA (genomic)

(ix) FEATURE:
        (A) NAME/KEY: CDS
        (B) LOCATION: 97..1389

(xi) SEQUENCE DESCRIPTION: SEQ ID NO:3:

-continued

| | | | | | | | | | | | | |
|---|---|---|---|---|---|---|---|---|---|---|---|---|
| GTGACCGAGC | GGCGCGGACG | GCCGCCTGCC | CCCTCTGCCA | CCTGGGGCGG | TGCGGGCCCG | | | | | | | 60 |
| GAGCCCGGAG | CCCGGGTAGC | GCGTAGAGCC | GGCGCG ATG | CAC GTG | CGC TCA | CTG | | | | | | 114 |
| | | | Met | His Val | Arg Ser | Leu | | | | | | |
| | | | 1 | | | 5 | | | | | | |

| CGA | GCT | GCG | GCG | CCG | CAC | AGC | TTC | GTG | GCG | CTC | TGG | GCA | CCC | CTG | TTC | 162 |
|---|---|---|---|---|---|---|---|---|---|---|---|---|---|---|---|---|
| Arg | Ala | Ala | Ala | Pro | His | Ser | Phe | Val | Ala | Leu | Trp | Ala | Pro | Leu | Phe | |
| | | | 10 | | | | | 15 | | | | | 20 | | | |

| CTG | CTG | CGC | TCC | GCC | CTG | GCC | GAC | TTC | AGC | CTG | GAC | AAC | GAG | GTG | CAC | 210 |
|---|---|---|---|---|---|---|---|---|---|---|---|---|---|---|---|---|
| Leu | Leu | Arg | Ser | Ala | Leu | Ala | Asp | Phe | Ser | Leu | Asp | Asn | Glu | Val | His | |
| | | | 25 | | | | | 30 | | | | | 35 | | | |

| TCG | AGC | TTC | ATC | CAC | CGG | CGC | CTC | CGC | AGC | CAG | GAG | CGG | CGG | GAG | ATG | 258 |
|---|---|---|---|---|---|---|---|---|---|---|---|---|---|---|---|---|
| Ser | Ser | Phe | Ile | His | Arg | Arg | Leu | Arg | Ser | Gln | Glu | Arg | Arg | Glu | Met | |
| | | | 40 | | | | | 45 | | | | | 50 | | | |

| CAG | CGC | GAG | ATC | CTC | TCC | ATT | TTG | GGC | TTG | CCC | CAC | CGC | CCG | CGC | CCG | 306 |
|---|---|---|---|---|---|---|---|---|---|---|---|---|---|---|---|---|
| Gln | Arg | Glu | Ile | Leu | Ser | Ile | Leu | Gly | Leu | Pro | His | Arg | Pro | Arg | Pro | |
| 55 | | | | | 60 | | | | | 65 | | | | | 70 | |

| CAC | CTC | CAG | GGC | AAG | CAC | AAC | TCG | GCA | CCC | ATG | TTC | ATG | CTG | GAC | CTG | 354 |
|---|---|---|---|---|---|---|---|---|---|---|---|---|---|---|---|---|
| His | Leu | Gln | Gly | Lys | His | Asn | Ser | Ala | Pro | Met | Phe | Met | Leu | Asp | Leu | |
| | | | | 75 | | | | | 80 | | | | | 85 | | |

| TAC | AAC | GCC | ATG | GCG | GTG | GAG | GAG | GGC | GGC | GGG | CCC | GGC | GGC | CAG | GGC | 402 |
|---|---|---|---|---|---|---|---|---|---|---|---|---|---|---|---|---|
| Tyr | Asn | Ala | Met | Ala | Val | Glu | Glu | Gly | Gly | Gly | Pro | Gly | Gly | Gln | Gly | |
| | | | 90 | | | | | 95 | | | | | 100 | | | |

| TTC | TCC | TAC | CCC | TAC | AAG | GCC | GTC | TTC | AGT | ACC | CAG | GGC | CCC | CCT | CTG | 450 |
|---|---|---|---|---|---|---|---|---|---|---|---|---|---|---|---|---|
| Phe | Ser | Tyr | Pro | Tyr | Lys | Ala | Val | Phe | Ser | Thr | Gln | Gly | Pro | Pro | Leu | |
| | | 105 | | | | | 110 | | | | | 115 | | | | |

| GCC | AGC | CTG | CAA | GAT | AGC | CAT | TTC | CTC | ACC | GAC | GCC | GAC | ATG | GTC | ATG | 498 |
|---|---|---|---|---|---|---|---|---|---|---|---|---|---|---|---|---|
| Ala | Ser | Leu | Gln | Asp | Ser | His | Phe | Leu | Thr | Asp | Ala | Asp | Met | Val | Met | |
| | 120 | | | | | 125 | | | | | 130 | | | | | |

| AGC | TTC | GTC | AAC | CTC | GTG | GAA | CAT | GAC | AAG | GAA | TTC | TTC | CAC | CCA | CGC | 546 |
|---|---|---|---|---|---|---|---|---|---|---|---|---|---|---|---|---|
| Ser | Phe | Val | Asn | Leu | Val | Glu | His | Asp | Lys | Glu | Phe | Phe | His | Pro | Arg | |
| 135 | | | | | 140 | | | | | 145 | | | | | 150 | |

| TAC | CAC | CAT | CGA | GAG | TTC | CGG | TTT | GAT | CTT | TCC | AAG | ATC | CCA | GAA | GGG | 594 |
|---|---|---|---|---|---|---|---|---|---|---|---|---|---|---|---|---|
| Tyr | His | His | Arg | Glu | Phe | Arg | Phe | Asp | Leu | Ser | Lys | Ile | Pro | Glu | Gly | |
| | | | | 155 | | | | | 160 | | | | | 165 | | |

| GAA | GCT | GTC | ACG | GCA | GCC | GAA | TTC | CGG | ATC | TAC | AAG | GAC | TAC | ATC | CGG | 642 |
|---|---|---|---|---|---|---|---|---|---|---|---|---|---|---|---|---|
| Glu | Ala | Val | Thr | Ala | Ala | Glu | Phe | Arg | Ile | Tyr | Lys | Asp | Tyr | Ile | Arg | |
| | | | 170 | | | | | 175 | | | | | 180 | | | |

| GAA | CGC | TTC | GAC | AAT | GAG | ACG | TTC | CGG | ATC | AGC | GTT | TAT | CAG | GTG | CTC | 690 |
|---|---|---|---|---|---|---|---|---|---|---|---|---|---|---|---|---|
| Glu | Arg | Phe | Asp | Asn | Glu | Thr | Phe | Arg | Ile | Ser | Val | Tyr | Gln | Val | Leu | |
| | | 185 | | | | | 190 | | | | | 195 | | | | |

| CAG | GAG | CAC | TTG | GGC | AGG | GAA | TCG | GAT | CTC | TTC | CTG | CTC | GAC | AGC | CGT | 738 |
|---|---|---|---|---|---|---|---|---|---|---|---|---|---|---|---|---|
| Gln | Glu | His | Leu | Gly | Arg | Glu | Ser | Asp | Leu | Phe | Leu | Leu | Asp | Ser | Arg | |
| | 200 | | | | | 205 | | | | | 210 | | | | | |

| ACC | CTC | TGG | GCC | TCG | GAG | GAG | GGC | TGG | CTG | GTG | TTT | GAC | ATC | ACA | GCC | 786 |
|---|---|---|---|---|---|---|---|---|---|---|---|---|---|---|---|---|
| Thr | Leu | Trp | Ala | Ser | Glu | Glu | Gly | Trp | Leu | Val | Phe | Asp | Ile | Thr | Ala | |
| 215 | | | | | 220 | | | | | 225 | | | | | 230 | |

| ACC | AGC | AAC | CAC | TGG | GTG | GTC | AAT | CCG | CGG | CAC | AAC | CTG | GGC | CTG | CAG | 834 |
|---|---|---|---|---|---|---|---|---|---|---|---|---|---|---|---|---|
| Thr | Ser | Asn | His | Trp | Val | Val | Asn | Pro | Arg | His | Asn | Leu | Gly | Leu | Gln | |
| | | | | 235 | | | | | 240 | | | | | 245 | | |

| CTC | TCG | GTG | GAG | ACG | CTG | GAT | GGG | CAG | AGC | ATC | AAC | CCC | AAG | TTG | GCG | 882 |
|---|---|---|---|---|---|---|---|---|---|---|---|---|---|---|---|---|
| Leu | Ser | Val | Glu | Thr | Leu | Asp | Gly | Gln | Ser | Ile | Asn | Pro | Lys | Leu | Ala | |
| | | | 250 | | | | | 255 | | | | | 260 | | | |

| GGC | CTG | ATT | GGG | CGG | CAC | GGG | CCC | CAG | AAC | AAG | CAG | CCC | TTC | ATG | GTG | 930 |
|---|---|---|---|---|---|---|---|---|---|---|---|---|---|---|---|---|
| Gly | Leu | Ile | Gly | Arg | His | Gly | Pro | Gln | Asn | Lys | Gln | Pro | Phe | Met | Val | |
| | | 265 | | | | | 270 | | | | | 275 | | | | |

| GCT | TTC | TTC | AAG | GCC | ACG | GAG | GTC | CAC | TTC | CGC | AGC | ATC | CGG | TCC | ACG | 978 |
|---|---|---|---|---|---|---|---|---|---|---|---|---|---|---|---|---|
| Ala | Phe | Phe | Lys | Ala | Thr | Glu | Val | His | Phe | Arg | Ser | Ile | Arg | Ser | Thr | |
| | 280 | | | | | 285 | | | | | 290 | | | | | |

| GGG | AGC | AAA | CAG | CGC | AGC | CAG | AAC | CGC | TCC | AAG | ACG | CCC | AAG | AAC | CAG | 1026 |
|---|---|---|---|---|---|---|---|---|---|---|---|---|---|---|---|---|
| Gly | Ser | Lys | Gln | Arg | Ser | Gln | Asn | Arg | Ser | Lys | Thr | Pro | Lys | Asn | Gln | |

-continued

| | | | | | | | | | | | | | | | | |
|---|---|---|---|---|---|---|---|---|---|---|---|---|---|---|---|---|
| 295 | | | | | 300 | | | | | 305 | | | | | 310 | |

| GAA | GCC | CTG | CGG | ATG | GCC | AAC | GTG | GCA | GAG | AAC | AGC | AGC | AGC | GAC | CAG | 1074 |
|---|---|---|---|---|---|---|---|---|---|---|---|---|---|---|---|---|
| Glu | Ala | Leu | Arg | Met | Ala | Asn | Val | Ala | Glu | Asn | Ser | Ser | Ser | Asp | Gln | |
| | | | | 315 | | | | 320 | | | | | 325 | | | |

| AGG | CAG | GCC | TGT | AAG | AAG | CAC | GAG | CTG | TAT | GTC | AGC | TTC | CGA | GAC | CTG | 1122 |
|---|---|---|---|---|---|---|---|---|---|---|---|---|---|---|---|---|
| Arg | Gln | Ala | Cys | Lys | Lys | His | Glu | Leu | Tyr | Val | Ser | Phe | Arg | Asp | Leu | |
| | | | | 330 | | | | 335 | | | | | 340 | | | |

| GGC | TGG | CAG | GAC | TGG | ATC | ATC | GCG | CCT | GAA | GGC | TAC | GCC | GCC | TAC | TAC | 1170 |
|---|---|---|---|---|---|---|---|---|---|---|---|---|---|---|---|---|
| Gly | Trp | Gln | Asp | Trp | Ile | Ile | Ala | Pro | Glu | Gly | Tyr | Ala | Ala | Tyr | Tyr | |
| | | | 345 | | | | 350 | | | | | 355 | | | | |

| TGT | GAG | GGG | GAG | TGT | GCC | TTC | CCT | CTG | AAC | TCC | TAC | ATG | AAC | GCC | ACC | 1218 |
|---|---|---|---|---|---|---|---|---|---|---|---|---|---|---|---|---|
| Cys | Glu | Gly | Glu | Cys | Ala | Phe | Pro | Leu | Asn | Ser | Tyr | Met | Asn | Ala | Thr | |
| | | 360 | | | | 365 | | | | | 370 | | | | | |

| AAC | CAC | GCC | ATC | GTG | CAG | ACG | CTG | GTC | CAC | TTC | ATC | AAC | CCG | GAA | ACG | 1266 |
|---|---|---|---|---|---|---|---|---|---|---|---|---|---|---|---|---|
| Asn | His | Ala | Ile | Val | Gln | Thr | Leu | Val | His | Phe | Ile | Asn | Pro | Glu | Thr | |
| 375 | | | | | 380 | | | | | 385 | | | | | 390 | |

| GTG | CCC | AAG | CCC | TGC | TGT | GCG | CCC | ACG | CAG | CTC | AAT | GCC | ATC | TCC | GTC | 1314 |
|---|---|---|---|---|---|---|---|---|---|---|---|---|---|---|---|---|
| Val | Pro | Lys | Pro | Cys | Cys | Ala | Pro | Thr | Gln | Leu | Asn | Ala | Ile | Ser | Val | |
| | | | | 395 | | | | 400 | | | | | 405 | | | |

| CTC | TAC | TTC | GAT | GAC | AGC | TCC | AAC | GTC | ATC | CTG | AAG | AAA | TAC | AGA | AAC | 1362 |
|---|---|---|---|---|---|---|---|---|---|---|---|---|---|---|---|---|
| Leu | Tyr | Phe | Asp | Asp | Ser | Ser | Asn | Val | Ile | Leu | Lys | Lys | Tyr | Arg | Asn | |
| | | | 410 | | | | 415 | | | | | 420 | | | | |

| ATG | GTG | GTC | CGG | GCC | TGT | GGC | TGC | CAC | TAGCTCCTCC | GAGAATTCAG | | | | | | 1409 |
|---|---|---|---|---|---|---|---|---|---|---|---|---|---|---|---|---|
| Met | Val | Val | Arg | Ala | Cys | Gly | Cys | His | | | | | | | | |
| | | 425 | | | | 430 | | | | | | | | | | |

ACCCTTTGGG GCCAAGTTTT TCTGGATCCT CCATTGCTC   1448

( 2 ) INFORMATION FOR SEQ ID NO:4:

( i ) SEQUENCE CHARACTERISTICS:
    ( A ) LENGTH: 431 amino acids
    ( B ) TYPE: amino acid
    ( D ) TOPOLOGY: linear ( i i ) MOLECULE TYPE: protein ( x i ) SEQUENCE DESCRIPTION: SEQ ID NO:4:

| Met | His | Val | Arg | Ser | Leu | Arg | Ala | Ala | Ala | Pro | His | Ser | Phe | Val | Ala |
|---|---|---|---|---|---|---|---|---|---|---|---|---|---|---|---|
| 1 | | | | 5 | | | | | 10 | | | | | 15 | |

| Leu | Trp | Ala | Pro | Leu | Phe | Leu | Leu | Arg | Ser | Ala | Leu | Ala | Asp | Phe | Ser |
|---|---|---|---|---|---|---|---|---|---|---|---|---|---|---|---|
| | | | 20 | | | | | 25 | | | | | 30 | | |

| Leu | Asp | Asn | Glu | Val | His | Ser | Ser | Phe | Ile | His | Arg | Arg | Leu | Arg | Ser |
|---|---|---|---|---|---|---|---|---|---|---|---|---|---|---|---|
| | | | 35 | | | | 40 | | | | | 45 | | | |

| Gln | Glu | Arg | Arg | Glu | Met | Gln | Arg | Glu | Ile | Leu | Ser | Ile | Leu | Gly | Leu |
|---|---|---|---|---|---|---|---|---|---|---|---|---|---|---|---|
| | 50 | | | | | 55 | | | | | 60 | | | | |

| Pro | His | Arg | Pro | Arg | Pro | His | Leu | Gln | Gly | Lys | His | Asn | Ser | Ala | Pro |
|---|---|---|---|---|---|---|---|---|---|---|---|---|---|---|---|
| 65 | | | | | 70 | | | | | 75 | | | | | 80 |

| Met | Phe | Met | Leu | Asp | Leu | Tyr | Asn | Ala | Met | Ala | Val | Glu | Glu | Gly | Gly |
|---|---|---|---|---|---|---|---|---|---|---|---|---|---|---|---|
| | | | | 85 | | | | | 90 | | | | | 95 | |

| Gly | Pro | Gly | Gly | Gln | Gly | Phe | Ser | Tyr | Pro | Tyr | Lys | Ala | Val | Phe | Ser |
|---|---|---|---|---|---|---|---|---|---|---|---|---|---|---|---|
| | | | 100 | | | | | 105 | | | | | 110 | | |

| Thr | Gln | Gly | Pro | Pro | Leu | Ala | Ser | Leu | Gln | Asp | Ser | His | Phe | Leu | Thr |
|---|---|---|---|---|---|---|---|---|---|---|---|---|---|---|---|
| | | 115 | | | | | 120 | | | | | 125 | | | |

| Asp | Ala | Asp | Met | Val | Met | Ser | Phe | Val | Asn | Leu | Val | Glu | His | Asp | Lys |
|---|---|---|---|---|---|---|---|---|---|---|---|---|---|---|---|
| | | 130 | | | | 135 | | | | | 140 | | | | |

| Glu | Phe | Phe | His | Pro | Arg | Tyr | His | His | Arg | Glu | Phe | Arg | Phe | Asp | Leu |
|---|---|---|---|---|---|---|---|---|---|---|---|---|---|---|---|
| 145 | | | | | 150 | | | | | 155 | | | | | 160 |

| Ser | Lys | Ile | Pro | Glu | Gly | Glu | Ala | Val | Thr | Ala | Ala | Glu | Phe | Arg | Ile |
|---|---|---|---|---|---|---|---|---|---|---|---|---|---|---|---|
| | | | | 165 | | | | | 170 | | | | | 175 | |

| Tyr | Lys | Asp | Tyr | Ile | Arg | Glu | Arg | Phe | Asp | Asn | Glu | Thr | Phe | Arg | Ile |

|  |  |  |  |  |  |  |  |  |  |  |  |  |  |  |
|---|---|---|---|---|---|---|---|---|---|---|---|---|---|---|
|  |  |  | 180 |  |  |  | 185 |  |  |  | 190 |  |  |  |
| Ser | Val | Tyr | Gln | Val | Leu | Gln | Glu | His | Leu | Gly | Arg | Glu | Ser | Asp | Leu |
|  |  |  | 195 |  |  |  | 200 |  |  |  | 205 |  |  |
| Phe | Leu | Leu | Asp | Ser | Arg | Thr | Leu | Trp | Ala | Ser | Glu | Glu | Gly | Trp | Leu |
|  |  |  | 210 |  |  |  | 215 |  |  |  | 220 |  |  |
| Val | Phe | Asp | Ile | Thr | Ala | Thr | Ser | Asn | His | Trp | Val | Val | Asn | Pro | Arg |
| 225 |  |  |  |  |  | 230 |  |  |  |  | 235 |  |  |  | 240 |
| His | Asn | Leu | Gly | Leu | Gln | Leu | Ser | Val | Glu | Thr | Leu | Asp | Gly | Gln | Ser |
|  |  |  |  | 245 |  |  |  |  | 250 |  |  |  |  | 255 |
| Ile | Asn | Pro | Lys | Leu | Ala | Gly | Leu | Ile | Gly | Arg | His | Gly | Pro | Gln | Asn |
|  |  |  | 260 |  |  |  |  | 265 |  |  |  |  | 270 |
| Lys | Gln | Pro | Phe | Met | Val | Ala | Phe | Phe | Lys | Ala | Thr | Glu | Val | His | Phe |
|  |  | 275 |  |  |  |  | 280 |  |  |  |  | 285 |
| Arg | Ser | Ile | Arg | Ser | Thr | Gly | Ser | Lys | Gln | Arg | Ser | Gln | Asn | Arg | Ser |
|  | 290 |  |  |  |  | 295 |  |  |  |  | 300 |
| Lys | Thr | Pro | Lys | Asn | Gln | Glu | Ala | Leu | Arg | Met | Ala | Asn | Val | Ala | Glu |
| 305 |  |  |  |  | 310 |  |  |  |  | 315 |  |  |  |  | 320 |
| Asn | Ser | Ser | Ser | Asp | Gln | Arg | Gln | Ala | Cys | Lys | Lys | His | Glu | Leu | Tyr |
|  |  |  |  | 325 |  |  |  |  | 330 |  |  |  |  | 335 |
| Val | Ser | Phe | Arg | Asp | Leu | Gly | Trp | Gln | Asp | Trp | Ile | Ile | Ala | Pro | Glu |
|  |  |  | 340 |  |  |  |  | 345 |  |  |  |  | 350 |
| Gly | Tyr | Ala | Ala | Tyr | Tyr | Cys | Glu | Gly | Glu | Cys | Ala | Phe | Pro | Leu | Asn |
|  |  | 355 |  |  |  |  | 360 |  |  |  |  | 365 |
| Ser | Tyr | Met | Asn | Ala | Thr | Asn | His | Ala | Ile | Val | Gln | Thr | Leu | Val | His |
|  | 370 |  |  |  |  | 375 |  |  |  |  | 380 |
| Phe | Ile | Asn | Pro | Glu | Thr | Val | Pro | Lys | Pro | Cys | Cys | Ala | Pro | Thr | Gln |
| 385 |  |  |  |  | 390 |  |  |  |  | 395 |  |  |  |  | 400 |
| Leu | Asn | Ala | Ile | Ser | Val | Leu | Tyr | Phe | Asp | Asp | Ser | Ser | Asn | Val | Ile |
|  |  |  |  | 405 |  |  |  |  | 410 |  |  |  |  | 415 |
| Leu | Lys | Lys | Tyr | Arg | Asn | Met | Val | Val | Arg | Ala | Cys | Gly | Cys | His |  |
|  |  |  | 420 |  |  |  |  | 425 |  |  |  |  | 430 |

OSTEOINDUCTIVE PHARMACEUTICAL FORMULATIONS

This invention relates to cartilage and/or bone inductive pharmaceutical formulations. More specifically, it relates to the use of epsilon aminocaproic acid (EACA) or other lysine analogues, serine protease inhibitors or other antifibrinolytic agents in cartilage and/or bone inductive formulations.

Formulations of the invention comprise EACA or other lysine analogues, serine protease inhibitors or antifibrinolytic agents in conjunction with cartilage and/or bone inductive proteins such as BMP-2 (having been designated in the past as BMP-2A or BMP-2 Class I), BMP-3, BMP-4 (having been designated in the past as BMP-2B and BMP-2 Class II) disclosed in International Publications WO88/00205 and WO89/10409. Further cartilage and/or bone inductive proteins for use in the invention include BMP-5, disclosed in SEQ ID NO:1 and SEQ ID NO:2; BMP-6, disclosed in allowed U.S. Ser. No. 490,033; and BMP-7, disclosed in SEQ ID NO:3 and SEQ ID NO:4. BMP-1 disclosed in U.S. Pat. No. 4,877,864 is another cartilage and/or bone inductive protein for use in formulations of the invention.

In further embodiments the formulations may further comprise growth factors such as epidermal growth factor (EGF), fibroblast growth factor (FGF), transforming growth factors (TGF-α and TGF-β), and platelet derived growth factor (PDGF).

The formulations may also include an appropriate matrix, for instance, for delivery and/or support of the composition and/or providing a surface for bone and/or cartilage formation. The matrix may provide slow release of the cartilage and/or osteoinductive protein(s) and/or the appropriate environment for presentation of the protein(s).

EACA is the presently preferred lysine analogue for use in formulations of the invention. The formulation may comprise other lysine analogues including trans-p-aminomethyl-cyclohexanecarboxylic acid (AMCA; tranexamic acid) (Amstat).

EACA is known to have a fibrin stabilizing effect. It inactivates plasmin which is a serine protease. [Nilsson et al Lancet, 1: 1322–1326 (1960)]. EACA has been shown to enhance new collagen synthesis in animals through blockage of the fibrinolytic system. [Brandstedt et al, Eur. Surg. Res. 12: 12–21 (1980)].

The invention further features a method for formulating the compositions of the invention, as well as use of the formulations in methods for treating a number of bone and/or cartilage defects, and periodontal disease. The formulations may also be employed in methods for treating various types of wounds and in tissue repair. These methods, according to the invention, entail administering a composition of the invention to a patient needing such bone and/or cartilage formation, wound healing or tissue repair. The method therefore involves administration of a therapeutically effective amount of a lysine analogue, serine protease inhibitor, or other antifibrinolytic agent and a therapeutically effective amount of a cartilage and/or bone inductive protein in a pharmaceutically acceptable carrier. These proteins include, for instance at least one of the "BMP" proteins disclosed in the co-owned applications described above.

In addition, these methods may further entail administration of other growth factors including EGF, FGF, TGF-α, TGF-β, and PDGF.

Other aspects and advantages of the invention will be apparent based upon consideration of the following detailed description and preferred embodiments thereof.

DETAILED DESCRIPTION OF THE INVENTION

The osteoinductive formulations of the invention comprise EACA, a lysine analogue (Amicar), in conjunction with a cartilage and/or bone inductive factor in a pharmaceutically acceptable vehicle. Other synthetic lysine analogues which may be used in practice of the invention include and trans-p-aminomethyl-cyclohexanecarboxylic acid (AMCA; tranexamic acid) (Amstat). Inhibitors of fibrin clot lysis, other than the lysine analogues mentioned above for instance serine protease inhibitors, in conjunction with a cartilage and/or bone inductive factor may also comprise formulations of the invention. Such serine protease inhibitors may include aprotinin, $\alpha_2$ antiplasmin and $\alpha_2$ macroglobulin. A further fibrinolytic agent which may be useful in formulations of the invention is p-amino methyl benzoic acid.

The cartilage and/or bone inductive factors which may be used in formulations of the invention include, but are not limited to BMP-2, BMP-3 and BMP-4 disclosed in International Publications WO88/00205 and WO89/10409. Further cartilage and/or bone inductive proteins for use in the invention include BMP-5, BMP-6, and BMP-7 disclosed respectively in BMP-5, disclosed in SEQ ID NO:1 and SEQ ID NO:2; BMP-6, disclosed in allowed U.S. Ser. No. 490,033; and BMP-7, disclosed in SEQ ID NO:3 and SEQ ID NO:4. BMP-1 disclosed in U.S. Pat. No. 4,877,864 may also be useful in formulations of the invention.

In addition to EACA and cartilage/bone protein, formulations of the invention further comprise autologous blood. At the time of surgery the matrix (described below) is mixed with a sufficient quantity of the patient's blood and EACA and cartilage/bone protein. The suitability of autologous blood is based on its biocompatability and ready availability. Autologous blood may also be utilized instead of another matrix.

In addition to the cartilage/bone protein, the formulations may include at least one other therapeutically useful agent including growth factors such as epidermal growth factor (EGF), fibroblast growth factor (FGF), transforming growth factors (TGF-α and TGF-β), and platelet derived growth factor (PDGF).

The formulations may also include an appropriate matrix, for instance, for delivery and/or support of the composition and/or providing a surface for bone and/or cartilage formation. The matrix may provide slow release of the BMP protein or other cartilage/bone protein or other factors of the formulation and/or the appropriate environment for presentation of the formulation of the invention. Preferably for bone and/or cartilage formation, the composition would include a matrix capable of delivering the cartilage and/or bone inductive proteins to the site of bone and/or cartilage damage, providing a structure for the developing bone and cartilage and optimally capable of being resorbed into the body. Such matrices may be formed of materials presently in use for other implanted medical applications.

The choice of matrix material is based on biocompatability, biodegradability, mechanical properties, cosmetic appearance and interface properties. The particular application of the formulations of the invention will define the appropriate formulation. Potential matrices for the compositions may be biodegradable and chemically defined calcium sulfate, tricalciumphosphate, hydroxyapatite, polylactic acid and polyanhydrides as well as coral. Other potential materials are biodegradable and biologically well defined, such as bone, tendon or dermal collagen. Further matrices are comprised of pure proteins or extracellular matrix components. Other potential matrices are nonbiodegradable and chemically defined, such as sintered hydroxyapatite, bioglass, aluminates, or other ceramics. Matrices may be comprised of combinations of any of the above mentioned types of material, such as polylactic acid and hydroxyapatite or collagen and tricalciumphosphate. The bioceramics may be altered in composition, such as in calcium-aluminate-phosphate and processing to alter pore size, particle size, particle shape, and biodegradability.

The formulations of the invention may be employed in methods for treating a number of bone and/or cartilage defects, and periodontal disease. They may also be employed in methods for treating various types of wounds and in tissue repair. These methods, according to the invention, entail administering a composition of the invention to a patient needing such bone and/or cartilage formation, wound healing or tissue repair. The method therefore involves administration of a lysine analogue and a therapeutically effective amount of a cartilage and/or bone inductive protein in a pharmaceutically acceptable vehicle. These methods may further include the administration of a protein of the invention with other growth factors including EGF, FGF, TGF-$\alpha$, TGF-$\beta$, and PDGF.

A formulation of the present invention, which induces cartilage and/or bone formation in circumstances where bone and/or cartilage is not normally formed, has application in the healing of bone fractures and cartilage defects in humans and other animals. A preparation employing lysine analogues such as EACA, serine protease inhibitors or other antifibrinolytic agents and a cartilage and/or bone inductive protein may have prophylactic use in closed as well as open fracture reduction and also in the improved fixation of artificial joints. De novo bone formation induced by an osteogenic agent contributes to the repair of congenital, trauma induced, or oncologic resection induced craniofacial defects, and also is useful in cosmetic plastic surgery. Formulations of the invention may be used in the treatment of periodontal disease, and in other tooth repair processes. Such formulations may provide an environment to attract bone-forming cells, stimulate growth of bone-forming cells or induce differentiation of progenitors of bone-forming cells.

The formulations of the invention may also be used in wound healing and related tissue repair. The types of wounds include, but are not limited to burns, incisions and ulcers. See, e.g. PCT Publication WO84/01106 for discussion of wound healing and related tissue repair.

The preparation of such physiologically acceptable formulations having due regard to pH, isotonicity, stability and the like, is within the skill of the art. The therapeutic formulations are also presently valuable for veterinary applications due to the apparent lack of species specificity in cartilage and bone growth factor proteins. Domestic animals and Thoroughbred horses in addition to humans are desired patients for such treatment with the proteins of the present invention.

The therapeutic method includes administering the formulation topically, systemically, or locally as an implant or device. When administered, the therapeutic formulation for use in this invention is, of course, in a pyrogen-free, physiologically acceptable form. Further, the formulation may desirably be encapsulated or injected in a viscous form for delivery to the site of cartilage and/or bone or tissue damage. Topical administration may be suitable for wound healing and tissue repair.

The dosage regimen will be determined by the attending physician considering various factors which modify the action of the formulation of the invention. Factors which may modify the action of the formulation include the amount of bone weight desired to be formed, the site of bone damage, the condition of the damaged bone, the size of a wound, type of damaged tissue, the patient's age, sex, and diet, the severity of any infection, time of administration and other clinical factors. The dosage may vary with the type of matrix used in the reconstitution and the type or types of bone and/or cartilage proteins present in the composition. The addition of other known growth factors, such as EGF, PDGF, TGF-$\alpha$, TGF-$\beta$, and IGF-I and IGF-II to the final composition, may also effect the dosage.

The concentration of EACA utilized in the sheep experiments described below is $10^{-3}$M. EACA is expected to have a wide margin of safety when used locally because up to 30 grams per 24 hours can be administered systemically without toxicity. [*Hemostasis and Thrombosis Basic Principles and Clinical Practice* pp. 380–384 (1988); Stefanini et al, *J. of Urology* 143: 559-561 (1990)].

Progress can be monitored by periodic assessment of cartilage and/or bone growth and/or repair. The progress can be monitored, for example, using x-rays, histomorphometric determinations and tetracycline labeling.

Other aspects and advantages of the present invention will be apparent upon consideration of the following detailed description and preferred embodiments thereof.

EXAMPLE I

Rosen Modified Sampath-Reddi Assay

A modified version of the rat bone formation assay described in Sampath and Reddi, *Proc. Natl. Acad. Sci. U.S.A.*, 80:6591-6595 (1983) is used to evaluate bone and/or cartilage activity of a formulation of the invention comprising EACA and cartilage and/or bone inductive proteins. This modified assay is herein called the Rosen Assay. The ethanol precipitation step of the Sampath-Reddi procedure is replaced by dialyzing (if the composition is a solution) or diafiltering (if the composition is a suspension) the fraction to be assayed against water. EACA is dissolved in water and added to 20 mg rat matrix wetted with 0.1% TFA and bone inductive protein. The controls include samples containing the bone inductive protein without the EACA. This material is frozen and lyophilized and the resulting powder enclosed in #5 gelatin capsules. The capsules are implanted subcutaneously in the abdominal thoracic area of 21-49 day old male Long Evans rats. The implants are removed after 7-14 days. Half of each implant is used for alkaline phosphatase analysis [See, A. H. Reddi et al., *Proc. Natl Acad Sci.*, 69:1601 (1972)].

The other half of each implant is fixed and processed for histological analysis. Glycolmethacrylate sections (1

μm) are stained with Von Kossa and acid fuschin or toluidine blue to score the amount of induced bone and cartilage formation present in each implant. The terms +1 through +5 represent the area of each histological section of an implant occupied by new bone and/or cartilage cells and newly formed bone and matrix. Two scoring methods are herein described. In the first scoring method a score of +5 indicates that greater than 50% of the implant is new bone and/or cartilage produced as a direct result of protein in the implant. A score of +4, +3, +2 and +1 would indicate that greater than 40%, 30%, 20% and 10% respectively of the implant contains new cartilage and/or bone. The second scoring method (which hereinafter may be referred to as the modified scoring method) is as follows: three non-adjacent sections are evaluated from each implant and averaged. "+/−" indicates tentative identification of cartilage or bone; "+1" indicates >10% of each section being new cartilage or bone; "+2", >25%; "+3", >50%; "+4", ~75%; "+5", >80%. The scores of the individual implants are tabulated to indicate assay variability.

As with other cartilage and/or bone inductive proteins such as the above-mentioned "BMP" proteins, the bone and/or cartilage formed is expected to be physically confined to the space occupied by the matrix. The implants containing rat matrix to which specific amounts of "BMP" protein or EACA and "BMP" protein have been added are removed from rats after approximately seven days and processed for histological evaluation. Representative sections from each implant are stained for the presence of new bone mineral with yon Kossa and acid fuschin, and for the presence of cartilage-specific matrix formation using toluidine blue. The types of cells present within the section, as well as the extent to which these cells display phenotype are evaluated and scored.

EXAMPLE II

Biological Activity of EACA and BMP-2 in the Rosen Assay

The efficacy of formulations of the invention comprising EACA and BMP-2 is tested in the Rosen Assay described above. The experiments include BMP-2, EACA and autologous blood, as well as BMP-2 and autologous blood without EACA. Negative controls without rat matrix include BMP-2 alone; BMP-2 and autologous blood and BMP-2 with autologous blood and EACA. EACA is dissolved in water and added to the rat matrix wetted with 0.1% TFA and BMP-2 [described in International Publication WO88/00205]. Amounts of EACA ranging from 13 μg to 6.9 mg are added per 20 mg of rat demineralized, guanidinium chloride extracted bone or from 1 mM to 0.5M based on a volume of 100 μg per implant. Samples are frozen and lyophilized and implanted in rats for seven days. The modified scoring method is utilized. In experiments containing autologous blood BMP-2 is mixed with the EACA and lyophilized in a siliconized glass tube. 100–200 ul of autologous blood is removed from the rat by orbital puncture and then added to the tube. The blood is allowed to clot for 1–2 hours; when firm, the clot is removed and implanted subcutaneously.

The amount of bone and/or cartilage formed increases with the use of EACA compared to samples lacking EACA when the same amount of cartilage/bone protein is utilized. The control samples do not result in any bone and/or cartilage formation. More specifically, in the presence of rat matrix, EACA increases the amount of bone formed as compared to BMP-2 without EACA at a moderate dose. EACA increases the amount of cartilage seen at a very low dose. Higher amounts of BMP-2 result in an increase of the amount of cartilage and bone (summed) formed and a more rapid appearance of bone.

Blood as a matrix dramatically increases the sensitivity of BMP-2 as compared to BMP-2 in the absence of blood. The recovery of any implant at all is quite small, in the absence of blood. The omission of EACA in these implants results in a lower recovery of activity and implants.

EXAMPLE III

Biological Activity of EACA and BMP-2 in a Sheep Model

An osteoperiosteal defect is created by excising a 2.5 cm midshaft segment from the right femur of skeletally mature sheep. Marrow contents and periosteum are removed from the exposed ends and the 2.5 cm gap stabilized with an anteriolateral metal fixation plate. Different materials are used to fill the gap in each of four groups of animals: (1) autologous bone graft from the cortical bone and iliac crest; (2) no implant ; (3) recombinant human BMP-2 , described above, mixed with inactive bone matrix comprising ground sheep bone demineralized and extracted with guanidinium chloride and the sterilized and EACA ; and (4) inactive bone matrix and EACA. The highly purified human BMP-2 , expressed in mammalian cells, is reconstituted with inactive bone matrix, is frozen and lyophilized. Following lyophilization blood is added and EACA added to a final concentration of 1 mM.

Femoral radiographs are performed weekly. Animals are sacrificed at 12 weeks post-op, and biomechanical testing [four-point bending to failure] followed by histological analysis is, performed on the limbs.

The untreated defect [group (2)] and the defect treated with inactive matrix [group (4)] failed to show radiographic healing by week 12. All defects treated with BMP-2 [group (3)] showed radiographic evidence of new bone formation beginning at week 5 and progressing to union by week 12. Defects treated with autologous graft [group (1)] also show union by week 12. The radiographic findings were confirmed by gross analysis: specimens from groups (2) and (4) examined at 12 weeks showed gross motion at a fibrous tissue seam across the segmental defect site, while the autologous graft and the BMP-2 treated sites were rigid. Biomechanical testing supported these results. At week 12, the average bending strength [expressed as a percentage of the contralateral intact femur] was 111% for autologous graft, 16% for groups (2) & (4), and 91% for defects treated with BMP-2 . Histologic analysis of a defect treated with BMP-2 showed evidence of new endochondral bone formation at two weeks post-op.

EXAMPLE IV

Rat Orthotopic Model

A 5 mm osteoperiosteal segmental defect (2×diaphyseal diameter) is created in the mid shaft of the femur of 325–350 gm Sprague-Dawley rats. Internal fixation is achieved with a four hole polyethylene plate fixed with 0.062 mm threaded Kirschnet wires. Marrow is flushed from the intramedullary cavity at each side of the osteotomy. Three groups of fifteen rats are studied as follows:

Group I: A rat matrix is implanted into the defect as a control.

Group II: A rat matrix, EACA and 1 μg microgm of BMP-2 is implanted as the low test dose.

Group III: A rat matrix, EACA and 8 μg microgm of BMP-2 is implanted as the high test dose.

EACA is added to 1 mM final concentration, assuming a volume of 50 ul, at the same time as the BMP-2 to the rat demineralized, guanidinium chloride-extracted bone. The sample is frozen and lyophilized. All rats are evaluated on day 7 for anglogenesis effect using dynamic quantitative bone scanning via intracardiac injection. The ratio of the total counts recorded over 60 seconds of the operated femur to the normal femur was then determined for each rat.

Bone formation in all rats is evaluated with serial radiographs taken at 1,2,3,4,5,6 and 9 weeks. The area of the defect occupied by bone is estimated by planimetry on lateral radiographs and recorded for each rat (as a percent of total defect area).

One rat is sacrificed each week for histologic analysis. Tissue from the grafted area and its surrounding bone is excised, decalcified, sectioned and stained with hematoxylin and eosin. Histological findings are recorded for sections taken parallel to the longitudinal axis of the bone extending over the entire length of the defect.

Those rats in which union occurred across the defect are subjected to mechanical torsion testing to failure to determine the maximum torque, angular displacement, energy absorption and stiffness of the operated femur with the results compared to the contralateral normal femur.

The foregoing descriptions detail presently preferred embodiments of the present invention. Numerous modifications and variations in practice thereof are expected to occur to those skilled in the art upon consideration of these descriptions. Those modifications and variations are believed to be encompassed within the claims appended hereto.

---

What is claimed is:

1. A pharmaceutical formulation consisting essentially of
   (a) an inhibitor of fibrin clot lysis selected from the group consisting of epsilon amino caproic acid, trans-p-amino methylcyclohexanecarboxylic acid, aprotinin, $\alpha_2$ antiplasmin, $\alpha_2$ macroglobulin, and p-amino methyl benzoic acid;
   (b) a therapeutically effective amount of an osteoinductive protein; and
   (c) autologous blood;
   admixed at the time of surgery in a pharmaceutically acceptable vehicle.

2. The formulation of claim 1, wherein said osteoinductive protein is selected from the group consisting of BMP-1, BMP-2, BMP-3, BMP-4, BMP-5 (SEQ ID NO:2), BMP-6, and BMP-7 (SEQ ID NO:4).

3. A pharmaceutical formulation consisting essentially of
   (a) an inhibitor of fibrin clot lysis selected from the group consisting of epsilon amino caproic acid, trans-p-amino methylcyclohexanecarboxylic acid, aprotinin, $\alpha_2$ antiplasmin, $\alpha_2$ macroglobulin, and p-amino methyl benzoic acid;
   (b) a therapeutically effective amount of an osteoinductive protein;
   (c) autologous blood; and
   (d) a pharmaceutically acceptable matrix selected from the group consisting of calcium sulfate, tricalciumphosphate, hydroxyapatite, and a lactic acid polymer;
   admixed at the time of surgery in a pharmaceutically acceptable vehicle.

4. A pharmaceutical formulation consisting essentially of
   (a) an inhibitor of fibrin clot lysis selected from the group consisting of epsilon amino caproic acid, trans-p-amino methylcyclohexanecarboxylic acid, aprotinin, $\alpha_2$ antiplasmin, $\alpha_2$ macroglobulin, and p-amino methyl benzoic acid;
   (b) a therapeutically effective amount of an osteoinductive protein;
   (c) autologous blood; and
   (d) a growth factor selected from the group consisting of IGF-I, IGF-II, PDGF, FGF, EGF, TGf-$\alpha$ and TGF-$\beta$; admixed at the time of surgery in a pharmaceutically acceptable vehichle.

5. A method for treating bone defects in a patient needing bone formation consisting essentially of administering to said patient a formulation consisting essentially of
   (a) an inhibitor of fibrin clot lysis selected from the group consisting of epsilon amino caproic acid, trans-p-amino-methylcyclohexanecarboxylic acid, aprotinin, $\alpha_2$ antiplasmin, $\alpha_2$ macroglobulin, and p-amino methyl benzoic acid;

(b) a therapeutically effective amount of an osteoinductive protein; and (c) autologous blood;

admixed at the time of surgery in a pharmaceutically acceptable vehicle, wherein a structure for developing bone and cartilage is provided.

6. The formulation of claim 2, wherein the inhibitor of fibrin clot lysis is epsilon amino caproic acid and the osteoinductive protein is BMP-2.

7. The method of claim 5, wherein the inhibitor of fibrin clot lysis is epsilon amino caproic acid.

* * * * *